US012703850B2

(12) United States Patent
Brinkmann et al.

(10) Patent No.: US 12,703,850 B2
(45) **Date of Patent: *Aug. 11, 2026**

(54) PHOTOSTABILIZED COMPOSITIONS AND A METHOD FOR STABILIZING PHOTOSENSITIVE COMPONENTS

(71) Applicant: Evonik Operations GmbH, Essen (DE)

(72) Inventors: Stephan Brinkmann, Giessen (DE); Martin Schilling, Bonn (DE); Anne Benedikt, Frankfurt (DE); Christina Jost, Alsbach-Hähnlein (DE); Tamara Heinze, Mainhausen (DE)

(73) Assignee: Evonik Operations GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/292,037

(22) PCT Filed: Dec. 7, 2022

(86) PCT No.: PCT/EP2022/084797

§ 371 (c)(1),
(2) Date: Jan. 25, 2024

(87) PCT Pub. No.: WO2023/217405

PCT Pub. Date: Nov. 16, 2023

(65) Prior Publication Data

US 2025/0064706 A1 Feb. 27, 2025

(30) Foreign Application Priority Data

May 12, 2022 (EP) .................................... 22172872

(51) Int. Cl.

| | |
|---|---|
| ***A61K 8/64*** | (2006.01) |
| ***A61K 47/18*** | (2017.01) |
| ***A61P 39/06*** | (2006.01) |
| ***A61Q 19/00*** | (2006.01) |
| ***C12N 5/00*** | (2006.01) |

(52) U.S. Cl.

CPC ............. *C12N 5/0018* (2013.01); *A61K 8/64* (2013.01); *A61K 47/183* (2013.01); *A61Q 19/00* (2013.01); *A61K 2800/10* (2013.01); *A61K 2800/522* (2013.01); *C12N 2500/30* (2013.01); *C12N 2500/32* (2013.01)

(58) Field of Classification Search

CPC .................. A61K 8/64; A61K 2800/52; A61K 2800/522; A61P 39/06; A61Q 19/00; C12N 2500/30; C12N 2500/32

See application file for complete search history.

(56) References Cited

U.S. PATENT DOCUMENTS

| | | | | |
|---|---|---|---|---|
| 5,034,377 | A | 7/1991 | Adibi et al. | |
| 2011/0262965 | A1* | 10/2011 | Barrett ................ | C12N 5/0018 435/235.1 |
| 2017/0058256 | A1 | 3/2017 | Barrett et al. | |
| 2019/0390161 | A1 | 12/2019 | Knaup et al. | |

OTHER PUBLICATIONS

International Search Report and Written Opinion issued Mar. 22, 2023, in PCT/EP2022/084797, filed on Dec. 7, 2022, 13 pages.
Janga et al. "Photostability Issues in Pharmaceutical Dosage Forms and Photostabilization", AAPS PharmSciTech, vol. 19, No. 1, Sep. 13, 2017 (Sep. 13, 2017), pp. 48-59.
Torkova et al. "Structure-Functional Study of Tyrosine and Methionine Dipeptides: An Approach to Antioxidant Activity Prediction", International Journal of Molecular Sciences, vol. 16, No. 10, Oct. 23, 2015 (Oct. 23, 2015), pp. 25353-25376.
Liu et al. "Influence of peptide bond on photosensitized oxidation of tryptophan, tyrosine and histidine dipeptides", Chinese Science Bulletin, vol. 42, No. 19, Oct. 19, 1997 (Oct. 19, 1997), pp. 1624-1628.
European Office Action issued Jun. 3, 2024 in European Application No. 22 830 847.4, 5 pgs.

* cited by examiner

*Primary Examiner* — Julie Ha
(74) *Attorney, Agent, or Firm* — Oblon, McClelland, Maier & Neustadt, L.L.P.

(57) ABSTRACT

Photostabilized compositions may include a water-soluble tyrosine-containing compound with a molecular weight of below 1 kDa and at least one photosensitive component. A method for stabilizing one or more photosensitive components may include the addition of a tyrosine-containing dipeptide with the one or more photosensitive components. The water-soluble tyrosine-comprising compound may be present at a concentration of at least 0.5 mM. The composition may be a culture medium.

19 Claims, 2 Drawing Sheets

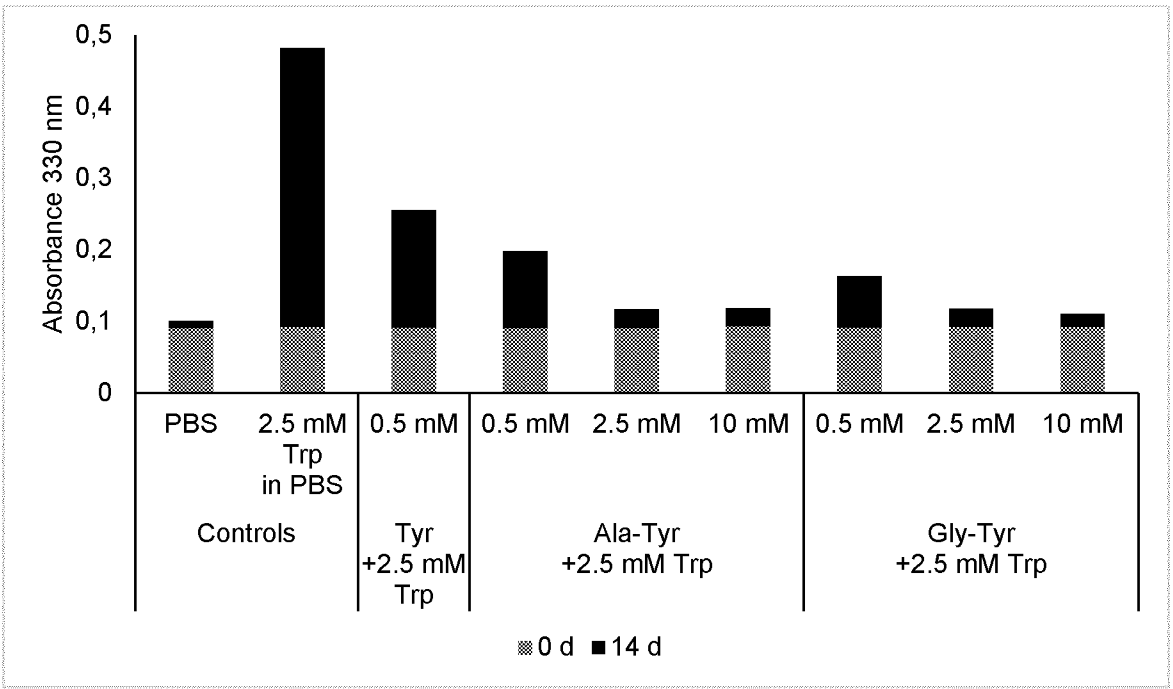
Figure 1: Effect on the brown colorization of different aqueous solutions containing Trp and Tyr-derivatives dissolved in phosphate-buffered saline (PBS) compared to controls of only PBS and Trp dissolved in PBS. The intensity of the brown color was measured as absorbance difference at 330 nm.

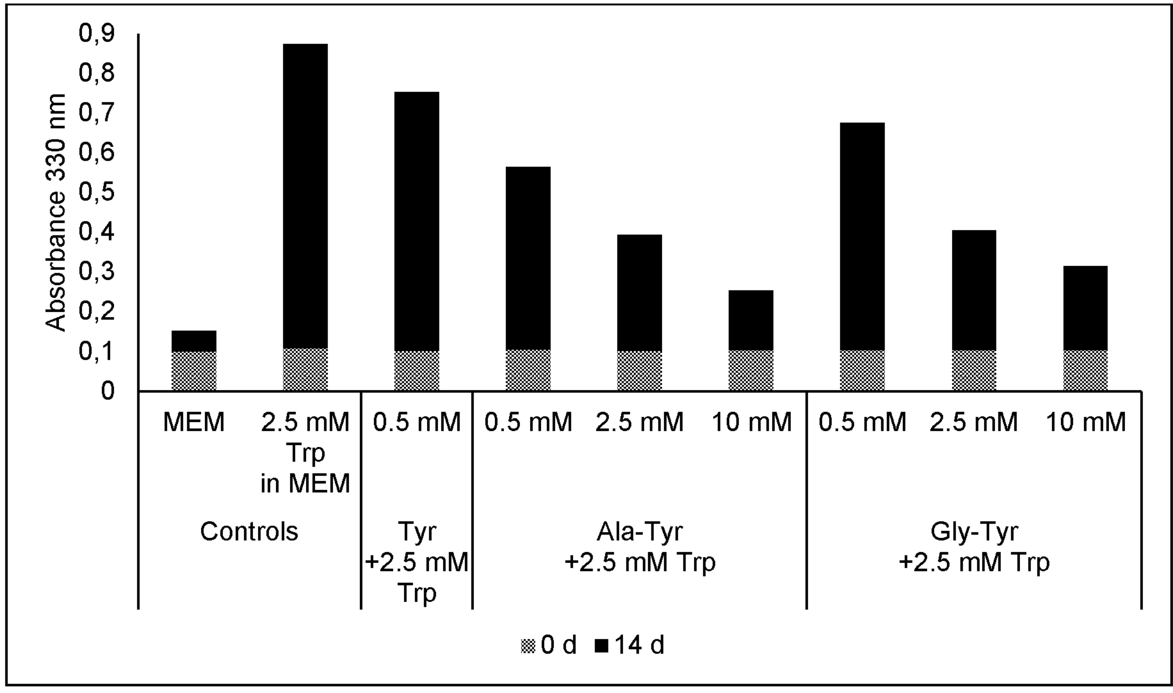
Figure 2: Effect on the brown colorization of different aqueous solutions containing Trp and Tyr-derivatives dissolved in Minimal Essential Medium (MEM) compared to controls of only MEM and Trp dissolved in MEM. The intensity of the brown color was measured as absorbance difference at 330 nm.

PHOTOSTABILIZED COMPOSITIONS AND A METHOD FOR STABILIZING PHOTOSENSITIVE COMPONENTS

CROSS-REFERENCE TO RELATED APPLICATIONS

The present application is the national stage of international application PCT/EP2022/084797, filed on Dec. 7, 2022, and claims the benefit of the filing date of European Appl. No. 22172872.8, filed on May 12, 2022.

BACKGROUND OF THE INVENTION

Field of the Invention

The present invention relates to photostabilized compositions comprising a water-soluble tyrosine-containing compound with a molecular weight of below 1 kDa and at least one photosensitive component and a method for stabilizing photosensitive components comprising the addition of a tyrosine-containing dipeptide.

Description of the Related Art

Many organic molecules are sensitive to electromagnetic radiation-induced degradation in the UV and visible spectrum. Examples comprise certain vitamins and amino acids but also macromolecules such as proteins that consist of amino acids or oligonucleotides such as DNA or mRNA. This poses a challenge to the use of those molecules, for example in pharmaceutical, nutritional, or cosmetic applications where product changes and degradation needs to be avoided to ensure safety and efficacy of the products.

Electromagnetic radiation either directly interacts with the photosensitive molecule resulting in degradation reactions or a photochemically exited molecule initiates various types of oxidation reactions, contributing to unwanted product formation or even degradation (Baptista et al., Photochemistry and Photobiology, 2021, 97: 1456-1483).

Many photosensitized oxidation reactions involve the formation of reactive oxygen species (ROS). ROS react with biomolecules, including DNA, lipids, and proteins as well as single amino acids. The photosensitivity of amino acids, especially Tryptophan (Trp), Tyrosine (Tyr), Histidine (His), Methionine (Met) and Cystine (Cys), has been investigated in detail. These molecules are photo-oxidized due to the combined action of light and oxygen, which cause oxidation and hydrolysis (Rumecal & McNeill, Environ. Sci Technol. 2011, 45: 5230-5237).

Photosensitivity of amino acids in protein drug product formulations is a not completely resolved problem. Limited photostability is also a challenge when formulating cell culture media. Amino acids are main components in cell culture media/feeds that are being used in biopharmaceutical manufacturing processes. During production, storage, transport, rehydration and/or the cell culture process itself (reaction vessels exposed to light), cell culture media/feeds can be unintentionally exposed to detrimental light. The photodegradation processes decompose sensitive media components such as amino acids, especially Trp, Tyr, His, Met and Cys, resulting in the accumulation of degradation products. This reactivity results in cell culture media/feeds instability and a change in color upon long-term storage. In this term, the process of unwanted cell culture medium/feed browning and the generation of toxic degradation products for cell lines is mainly facilitated by Trp (Schnellbaecher et al., Int. J. Mol. Sci. 2021, 22: 6221).

Cell culture media/feeds are mixtures of various components, including photosensitizers such as riboflavin (vitamin B2). Photosensitizers favor photosensitized oxidation reactions of sensitive cell culture medium/feed compounds with the most sensitive ones being the amino acids Trp and Tyr (Wu & McCormick, Biochim. Biophys. Acta 1971, 236: 479-486).

Molecules in solution are especially sensitive and need to be protected from light by storing them in the dark or using appropriate packaging. As this is not always possible, photostabilizers and radical scavengers have been developed for various applications where products are exposed to light (plastics etc.) (Yousif & Haddad, SpringerPlus 2013, 2: 398).

However, when it comes to cosmetic, nutritional, or pharmaceutical formulations that are in direct contact with the body or with isolated cells and tissues, it's important that the photostabilizers are highly biocompatible, non-toxic, and ideally easily metabolized (Kawabata et al., Pharmaceuticals 2020, 13: 135).

Amino acids can fulfil that function to a certain extent but not completely.

Thus, there remains a need for improved photostabilizers to stabilize light sensitive components in nutritional, cosmetic, cell culture media/feed and drug product formulations. Therefore, it was a goal of the present invention to provide a method for stabilizing photosensitive components in aqueous solution, especially photosensitive amino acids.

BRIEF SUMMARY OF THE INVENTION

Surprisingly, it was found that the addition of tyrosine derivatives to aqueous solutions containing tryptophan or riboflavin and to cell culture media/feeds reduces or even prevents their browning and thus contributes to photostabilization. Especially, the addition of Tyr-dipeptides resulted in decreased color formation.

The present invention is therefore directed to a photostabilized composition comprising a water-soluble tyrosine-containing compound with a molecular weight of below 1 kDa and at least one photosensitive component, wherein the water-soluble tyrosine-containing compound is present at a concentration of at least 0.5 mM and wherein the composition is a culture medium.

In a preferred embodiment, the culture medium is a cell culture medium selected from a basal medium, feed medium or perfusion medium.

The present invention is moreover directed to a method for stabilizing photosensitive components, comprising the addition of a tyrosine-containing dipeptide selected from Xxx-Tyr or Tyr-Xxx, wherein Xxx is a natural amino acid, wherein the dipeptide is present at a concentration of at least 0.5 mM.

Another aspect of the present invention relates to the use of tyrosine-containing dipeptide for stabilizing photosensitive components in cell culture, cosmetics, food applications, parenteral nutrition or drug products formulations.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 shows the effect on the brown colorization of different aqueous solutions containing Trp and Tyr-derivatives dissolved in phosphate-buffered saline (PBS) compared to controls of only PBS and Trp dissolved in PBS; and FIG. 2 shows the effect on the brown colorization of different aqueous solutions containing Trp and Tyr-derivatives dissolved in Minimal Essential Medium (MEM) compared to controls of only MEM and Trp dissolved in MEM.

DETAILED DESCRIPTION OF THE INVENTION

Preferred embodiments of the invention are described in further detail in the following detailed description of the invention.

A "peptide" shall be understood as being a molecule comprising at least two amino acids covalently coupled to each other by alpha-peptide bonds (R1-CO—NH—R2).

A "dipeptide" shall be understood as being a molecule comprising two amino acids covalently coupled to each other by a peptide-bond (R1-CO—NH—R2) it may also be present as a salt or in hydrate form.

An "amino acid", in the context of the present invention, shall be understood as being a molecule comprising an amino functional group (—NH2) and a carboxylic acid functional group (—COOH), along with a side-chain specific to the respective amino acid. In the context of the present invention, both alpha- and beta-amino acids are included. Preferred amino acids of the invention are alpha-amino acids, in particular the 20 "natural amino" acids including cystine as follows:

Alanine (Ala/A)
Arginine (Arg/R)
Asparagine (Asn/N)
Aspartic acid (Asp/D)
Cysteine (Cys/C)
Cystine (Cyss/C2)
Glutamic acid (Glu/E)
Glutamine (Gln/Q)
Glycine (Gly/G)
Histidine (His/H)
Isoleucine (Ile/I)
Leucine (Leu/L)
Lysine (Lys/K)
Methionine (Met/M)
Phenylalanine (Phe/F)
Proline (Pro/P)
Serine (Ser/S)
Threonine (Thr/T)
Tryptophan (Trp/W)
Tyrosine (Tyr/Y)
Valine (Val/V)

In the context of the present invention, the expression "natural amino acids" shall be understood to include both the L-form and the D-form of the above listed 20 amino acids. The L-form, however, is preferred. In one embodiment, the term "amino acid" also includes analogues or derivatives of those amino acids.

A "free amino acid", according to the invention (for instance "free cysteine"), is understood as being an amino acid having its amino and its (alpha-) carboxylic functional group in free form, i.e., not covalently bound to other molecules, e.g., an amino acid not forming a peptide bond. Free amino acids may also be present as salts or in hydrate form. When referring to an amino acid as a part of, or in, a dipeptide, this shall be understood as referring to that part of the respective dipeptide structure derived from the respective amino acid, according to the known mechanisms of biochemistry and peptide biosynthesis.

A "growth factor", according to the invention, shall be understood as being any naturally occurring substance capable of stimulating cellular growth, proliferation and cellular differentiation. Preferred growth factors are in form of protein or steroid hormone. According to one embodiment of the invention, the expression "growth factor" shall be interpreted as relating to a growth factor selected from the list consisting of fibroblast growth factor (FGF), including acidic FGF and basic FGF, insulin, insulin-like growth factor (IGF), epithelial growth factor (EGF), nerve growth factor (NGF), platelet-derived growth factor (PDGF), and transforming growth factor (TGF), including TGFalpha and TGFbeta, cytokine, such as interleukins 1, 2, 6, granulocyte stimulating factor, and leukocyte inhibitory factor (LIF).

A "culture medium", according to the invention, shall be understood as being a liquid or solid medium containing nutrients, the medium being suitable for nourishing and supporting life and/or product formation of cells in the culture, excluding media for parenteral nutrition. The cultured cells, according to the invention, may be bacterial cells, yeast cells, fungal cells, animal cells, such as mammalian cells or insect cells, and/or plant cells, e.g., algae. Typically, a culture medium provides essential and non-essential amino acids, vitamins, at least one energy source, lipids, and trace elements, all required by the cell for sustaining life, growth and/or product formation. The culture medium may also contain components that enhance growth and/or survival above the minimal rate, including hormones and growth factors. The culture medium has preferably a pH and a salt concentration which supports life, growth and/or product formation of the cells. A culture medium, according to the invention, preferably comprises all nutrients necessary to sustain life and proliferation of the cell culture. Preferred culture media are defined media.

A "chemically defined medium", according to the invention is a medium that contains no cell extracts, cell hydrolysates, or protein hydrolysates. Chemically defined media comprise no components of unknown composition. As is commonly understood by the person skilled in the art, chemically defined media are usually free of animal-derived components. All components of a chemically defined medium have a known chemical structure. Culture media other than defined culture media may be referred to as "complex" culture media.

A "cell culture medium" shall be understood as being a culture medium suitable for sustaining life, proliferation and/or product formation of animal cells and/or plant cells.

A "basal medium" or "basal culture medium" shall be understood as being a solution or substance containing nutrients in which a culture of cells is initiated.

A "feed medium" shall be understood as being a solution or substance with which the cells are fed after the start of the cultivation process. In certain embodiments, a feed medium contains one or more components not present in a basal medium. The feed medium can also lack one or more components present in a basal medium. Preferably, the concentration of nutrients in the feed medium exceeds the concentration in the basal medium to avoid a loss of productivity by dilution.

A "perfusion medium" shall be understood as being a solution or substance containing nutrients that is continuously added after the beginning of a cell culture, in which harvest is continuously removed.

The compositions and the method according to the present invention enhances photostability of photosensitive components. One negative aspect of limited photostability is brown color formation e.g., facilitated by tryptophan. In this context, photostability can be characterized by for example color-change under exposure to day light.

In a preferred configuration, the water-soluble tyrosine-containing compound is present at a concentration of at least 1 mM, or at least 2 mM, or at least 5 mM, or at least 10 mM, or at least 20 mM.

In another preferred embodiment, the water-soluble tyrosine-containing compound is selected from phospho-tyrosine or a dipeptide, preferably Ala-Tyr or Gly-Tyr.

In another preferred embodiment, the photosensitive component is selected form aromatic compounds, preferably selected from riboflavin and aromatic amino acids or derivatives thereof, preferably selected from tryptophan and tyrosine.

In a preferred configuration of the present invention, the cell culture medium further comprises free tyrosine.

The photosensitive components according to the present invention are selected from aromatic compounds, preferably selected from riboflavin and aromatic amino acids or derivatives thereof, preferably selected from tryptophan and tyrosine. Those components are known to contribute to color-formation under light exposure.

In a preferred configuration, the derivatives of aromatic amino acids are soluble derivatives of tryptophan or tyrosine, preferably selected from phospho-tyrosine.

In a specific configuration of the present invention, the photosensitive component is present in an amount of at least 0.5 mM, preferably at least 1 mM, more preferably at least 2 mM.

Another aspect of the present invention relates to a method for stabilizing photosensitive components.

In a preferred embodiment of the method according to the present invention, the photosensitive component is present in aqueous solution.

In another preferred embodiment, the dipeptide is selected from Ala-Tyr or Gly-Tyr.

In another preferred embodiment, the photosensitive component is selected form aromatic compounds, preferably selected from riboflavin and aromatic amino acids or derivatives thereof, preferably selected from tryptophan and tyrosine, more preferably tryptophan.

In another preferred configuration of the method according to the present invention, a molar ratio of the dipeptide to tryptophan is from about 10:1 to 1:10, preferably from about 5:1 to 1:5.

In another preferred embodiment, the dipeptide is added to the aqueous solution at a concentration of at least 1 mM, or at least 2 mM or at least 5 mM or at least 10 mM or at least 20 mM.

In another preferred embodiment, a cysteine derivative is added, preferably selected from a cysteine containing dipeptide or a cysteine salt, preferably a S-sulfate sodium salt of cysteine.

In another preferred embodiment, the aqueous solution is a cell culture medium, and the cultured cells are cultivated in presence of the tyrosine-containing dipeptide.

Cultivation of cells, according to the invention can be performed in batch culture, in fed-batch culture or in continuous culture.

In a preferred embodiment, the culture medium further comprises at least one carbohydrate, at least one free amino acid, at least one inorganic salt, a buffering agent and/or at least one vitamin.

In one embodiment of the invention, the culture medium does not contain growth factors. In accordance with this embodiment, the dipeptide of the invention may be used instead of a growth factor for promoting growth and/or proliferation of the cells in culture. In another embodiment of the invention, the culture medium does not contain any lipids.

In preferred embodiments, the culture medium of the invention is a defined medium, or a serum-free medium. For example, the compositions of the intervention may be supplemented to the Freestyle™ F17 medium, the Freestyle™ 293 medium, the Expi293™ medium all of Gibco™ ThermoFisher (Waltham, USA), the TheraPEAK™ SfAAV™ Medium of LONZA (Basel, Switzerland), the HEK ViP NB of Sartorius Xell (Bielefeld, Germany), HyClone™ SFM4HEK293 of Cytiva (Marlborough, USA). The dipeptides of the invention may also be supplemented to DMEM medium (Life Technologies Corp., Carlsbad, USA). The invention, however, is not limited to supplementation of the above media.

The cell culture medium (cell or tissue culture basal, feed or perfusion medium) of the present invention may preferably contain all nutrients required for sustained growth and product formation. Recipes for preparing culture media, in particular cell culture media, are well known to the person skilled in the art (see, e.g., Cell Culture Technology for Pharmaceutical and Cell-Based Therapies, Öztürk and Wei-Shou Hu eds., Taylor and Francis Group 2006). Various culture media are commercially available from various sources.

The culture media of the invention may preferably include a carbohydrate source. The main carbohydrate used in cell culture media is glucose, routinely supplemented at 5 to 25 mM. In addition, any hexose, such as galactose, fructose, or mannose or a combination may be used.

The culture medium typically may also include at least the essential amino acids (i.e., His, Ile, Leu, Lys, Met, Phe, Thr, Try, Val) as well as non-essential amino acids. A non-essential amino acid is typically included in the cell culture medium if the cell line is not capable of synthesizing the amino acid or if the cell line cannot produce sufficient quantities of the amino acid to support maximal growth. In addition, mammalian cells can also use glutamine as a major energy source. Glutamine is often included at higher concentrations than other amino acids (2-8 mM). However, as noted above, glutamine can spontaneously break down to form ammonia and certain cell lines produce ammonia faster, which is toxic.

The culture media of the invention may preferably comprise salts. Salts are added to the cell culture medium to maintain isotonic conditions and prevent osmotic imbalances. The osmolality of a culture medium of the invention is about 300 mOsm/kg, although many cell lines can tolerate an approximately 10 percent variation of this value or higher. The osmolality of some insect cell cultures tends to be higher than 300 mOsm/kg, and this may be 0.5 percent, 1 percent, 2 to 5 percent, 5-10 percent, 10-15 percent, 15-20 percent, 20-25 percent, 25-30 percent higher than 300 mOsm/kg. The most commonly used salts in cell culture medium include Na+, K+, Mg2+, Ca2+, Cl−, SO42−, PO43−, and HCO3− (e.g., CaCl2, KCl, NaCl, NaHCO3, Na2HPO4).

Other inorganic elements may be present in the culture medium. They include Mn, Cu, Zn, Mo, Va, Se, Fe, Ca, Mg, Si, and Ni. Many of these elements are involved in enzymatic activity. They may be provided in the form of salts such as CaCl2, Fe(NO3)3, MgCl2, MgSO4, MnCl2, NaCl, NaHCO3, Na2HPO4, and ions of the trace elements, such as, selenium, vanadium and zinc. These inorganic salts and trace elements may be obtained commercially, for example from Sigma (Saint Louis, Missouri).

The culture media of the invention preferably comprise vitamins. Vitamins are typically used by cells as cofactors. The vitamin requirements of each cell line vary greatly, although generally extra vitamins are needed if the cell culture medium contains little or no serum or if the cells are grown at high density. Exemplary vitamins preferably present in culture media of the invention include biotin, choline chloride, folic acid, i-inositol, nicotinamide, D-Ca++-pantothenate, pyridoxal, riboflavin, thiamine, pyridoxine, niacinamide, A, B6, B12, C, D3, E, K, and p-aminobenzoic acid (PABA).

Culture media of the invention may also comprise serum. Serum is the supernatant of clotted blood. Serum components include attachment factors, micronutrients (e.g., trace elements), growth factors (e.g., hormones, proteases), and protective elements (e.g., antitoxins, antioxidants, antiproteases). Serum is available from a variety of animal sources including human, bovine or equine serum. When included in cell culture medium according to the invention, serum is typically added at a concentration of 5-10% (vol.). Preferred cell culture media are serum-free.

One or more lipids can also be added to a cell culture medium of the invention, such as linoleic acid, linolenic acid, arachidonic acid, palmitoleic acid, oleic acid, polyenoic acid, and/or fatty acids of 12, 14, 16, 18, 20, 22, or 24 carbon atoms, each carbon atom branched or unbranched, phospholipids, lecithin (phosphatidylcholine), and cholesterol. One or more of these lipids can be included as supplements in serum-free media. Phosphatidic acid and lysophosphatidic acid stimulate the growth of certain anchorage-dependent cells, such as MDCK, mouse epithelial, and other kidney cell lines, while phosphatidylcholine, phosphatidylethanolamine, and phosphatidylinositol stimulate the growth of human fibroblasts in serum-free media. Ethanolamine and cholesterol have also been shown to promote the growth of certain cell lines. In certain embodiment, the cell culture medium does not contain a lipid.

One or more carrier proteins, such as bovine serum albumin (BSA) or transferrin, can also be added to the cell culture medium. Carrier proteins can help in the transport of certain nutrients or trace elements. BSA is typically used as a carrier of lipids, such as linoleic and oleic acids, which are insoluble in aqueous solution. In addition, BSA can also serve as a carrier for certain metals, such as Fe, Cu, and Ni. In protein-free formulations, non-animal derived substitutes for BSA, such as cyclodextrin, can be used as lipid carriers.

One or more attachment proteins, such as fibronectin, laminin, and pronectin, can also be added to a cell culture medium to help promote the attachment of anchorage-dependent cells to a substrate.

The cell culture medium can optionally include one or more buffering agents. Suitable buffering agents include, but are not limited to, N-[2-hydroxyethyl]-piperazine-N'-[2-ethanesulfonic acid] (HEPES), MOPS, MES, phosphate, bicarbonate and other buffering agents suitable for use in cell culture applications. A suitable buffering agent is one that provides buffering capacity without substantial cytotoxicity to the cells cultured. The selection of suitable buffering agents is within the ambit of ordinary skill in the art of cell culture.

Polyanionic or polycationic compounds may be added to the culture medium to prevent the cells from clumping and to promote growth of the cells in suspension.

In a preferred embodiment, the culture medium is in liquid form. The culture medium, however, can also be a solid medium, such as a gel-like medium, e.g., an agar-agar-, carrageen- or gelatine-containing medium (powders, aggregated powders, instantized powders etc.). Preferably, the culture medium is in sterile form.

The culture medium of the present invention can be in concentrated form. It may be, e.g., in 2- to 100-fold concentrated form, preferably in 2-fold, 3-fold, 3.33-fold, 4-fold, 5-fold, 10-fold, 20-fold, 50-fold or 100-fold (relative to a concentration that supports growth and product formation of the cells). Such concentrated culture media are helpful for preparing the culture medium for use by dilution of the concentrated culture medium with an aqueous solvent, such as water. Such concentrated culture media may be used in batch culture but are also advantageously used in fed-batch or continuous cultures, in which a concentrated nutrient composition is added to an ongoing cultivation of cells, e.g., to replenish nutrients consumed by the cells during culture.

In other embodiments of the invention, the culture medium is in dry form, e.g., in form of a dry powder, or in form of granules, or in form of pellets, or in form of tablets.

Another aspect of the present invention relates to the use of tyrosine-containing dipeptides for stabilizing photosensitive components in cell culture, cosmetics, food applications, parenteral nutrition or drug products formulations.

In a preferred configuration, the use is in a cell culture medium for stabilizing photosensitive components in cell culture, preferably as a basal medium, feed medium or perfusion medium.

In a preferred embodiment, the cells are selected from the list consisting of CHO cells, COS cells, VERO cells, BHK cells, HEK cells, HELA cells, AE-1 cells, NS0 cells, insect cells, algae cells, fibroblast cells, muscle cells, nerve cells, stem cells, skin cells, endothelial cells, immune cells such as NK or T-cells and hybridoma cells.

EXAMPLES

Material

TABLE 1

Material used for radiation tests.

| Material | Supplier |
|---|---|
| L-tryptophane (Trp) | Evonik rexim S.A.S., Ham (France) |
| L-tyrosine (Tyr) | Sigma-Aldrich, Missouri (USA) |
| Glycine (Gly) | Evonik rexim S.A.S., Ham (France) |
| L-alanine (Ala) | Evonik rexim S.A.S., Ham (France) |
| (−)-Riboflavin | Sigma-Aldrich, Missouri (USA) |

TABLE 1-continued

| Material used for radiation tests. | |
|---|---|
| Material | Supplier |
| $_L$-alanyl-$_L$-tyrosine dihydrate (Ala-Tyr) | Evonik Operations GmbH, Darmstadt (Germany) |
| glycyl-$_L$-tyrosine dihydrate (Gly-Tyr) | Evonik Operations GmbH, Darmstadt (Germany) |
| 50 mL centrifuge tubes, clear | Greiner Bio-One, Kremsmünster (Austria) |
| 50 mL centrifuge tubes, brown | Greiner Bio-One, Kremsmünster (Austria) |
| 2 mL safe-lock tubes, brown | Eppendorf, Hamburg (Germany) |
| 96-well plates, transparent, flat bottom | Greiner Bio-One, Kremsmünster (Austria) |
| 0.22 μm syringe filter | Corning, Kaiserslautern (Germany) |
| 50 mL single-use syringe, luer lock solo | Braun, Melsungen (Germany) |
| D-PBS, no calcium, no magnesium | Invitrogen, Carlsbad (USA) |
| Minimum essential medium (MEM) | Invitrogen, Carlsbad (USA) |
| Aluminum foil | Carl Roth, Karlsruhe (Germany) |
| Bottle top sterile filter | Thermo scientific, Massachusetts (USA) |

TABLE 2

| Devices used for radiation tests. | |
|---|---|
| Safety cabinet HERA Safe 2020 | Thermo Fisher Scientific GmbH, Dreieich (Germany) |
| Centrifuge 5415R | Eppendorf, Hamburg (Germany) |
| TECAN Infinite 200 Pro | Tecan Group Ltd., Männedorf (Switzerland) |
| Analytical Balance, ME215S-0CE | Sartorius AG, Göttingen (Germany) |
| Analytical Balance, AC211S-OCEMS | Sartorius AG, Göttingen (Germany) |
| Eppendorf Pipets | Eppendorf, Hamburg (Germany) |
| −20° C. Freezer, GN 3056 | Liebherr-Hausgeräte GmbH, Ochesenhausen (Germany) |
| Refrigerator, Aqualytic AL656 | Tintometer GmbH, Dortmund (Germany) |

Methods

Preparation of Test Samples

Aqueous solutions of 2.5 mM L-Tryptophan (Trp) and 0.013 mM riboflavin were prepared in phosphate-buffered saline (D-PBS) as well as in Minimal Essential Medium (MEM). These solutions were used to dissolve the dipeptides L-alanyl-L-tyrosine dihydrate (Ala-Tyr) and glycyl-L-tyrosine dihydrate (Gly-Tyr) as well as the amino acids L-tyrosine (Tyr), L-alanine (Ala), and glycine (Gly) at several concentrations to create solvent mixtures. In example 1, the dipeptides were tested at concentrations of 0.5 mM, 2.5 mM and 10 mM and Tyr at a concentration of 0.5 mM. PBS and MEM as well as 2.5 mM Trp dissolved in PBS and MEM were used as controls. In example 2, the dipeptides and Tyr were tested at a concentration of 2 mM, Ala and Gly at 32 mM, and the solvent (PBS or MEM) was used as control ("solvent background").

Detection of Brown Color

The samples were exposed to electromagnetic radiation (day light) at room temperature for seven (example 2) as well as 14 days (example 1). A relative quantification of the brown color of the samples of example 1 was obtained by measuring the absorbance at 330 nm. The intensity of the brown color of samples of example 2 was determined by eye using a brown color index. The numbers one to five correspond to the intensity of the brown color of the solutions (0, no brown color; 1, week brown color; 2, moderate brown color; 3, normal brown color; 4, intensive brown color; 5, strong brown color).

Example 1: Reduced Brown Color of Tryptophan Solutions Containing Tyr-Derivatives Exposure of an uncolored aqueous solution of PBS or MEM containing 2.5 mM Trp to electromagnetic radiation at room temperature leads to a strong color change towards brown color. The addition of 0.5 mM Tyr or Tyr-dipeptide (Ala-Tyr or Gly-Tyr) has been shown to reduce this colorization, especially with both Tyr-dipeptides the effect is greater. Concentrations of dipeptides of up to 10 mM are above the solubility of Tyr and resulted in further reduction or even completely prevented the change in color. The results are depicted in FIG. 1 and FIG. 2.

FIG. 1 shows the effect on the brown colorization of different aqueous solutions containing Trp and Tyr-derivatives dissolved in phosphate-buffered saline (PBS) compared to controls of only PBS and Trp dissolved in PBS. The intensity of the brown color was measured as absorbance difference at 330 nm.

FIG. 2 shows the effect on the brown colorization of different aqueous solutions containing Trp and Tyr-derivatives dissolved in Minimal Essential Medium (MEM) compared to controls of only MEM and Trp dissolved in MEM. The intensity of the brown color was measured as absorbance difference at 330 nm.

Example 2: Reduced Brown Color of Riboflavin Solutions Containing Tyr-Derivatives Aqueous solutions of PBS or MEM containing 0.013 mM riboflavin show a week fluorescent yellow-green color. Exposure to electromagnetic radiation at room temperature for seven days results in a brown colorization of the MEM solution, while the yellow-green color in PBS solutions vanished. The intensity of the brown color was classified as 'normal brown color' based on the applied brown color index.

Similar, control solutions of MEM with 0.013 mM riboflavin and additionally added amino acids such as Ala and Gly at a concentration of up to 32 mM also turned 'normal brown' in color, while the same control solutions in PBS stayed colorless. Other control solutions of PBS and MEM without riboflavin were colorless at day 0. After seven days of electromagnetic radiation at room temperature, the PBS solution stayed colorless while the MEM solution turned 'week brown' in color. The same was observed for control solutions without riboflavin and additionally added amino acids such as Ala and Gly at a concentration of up to 32 mM.

The addition of an aromatic amino acid such as Tyr (2 mM) to any type of aqueous solution used, in combination with an exposition to electromagnetic radiation at room temperature for seven days, was found to result in a 'strong brown' colorization of all solutions. Interestingly, compared to this 'strong brown color', an equimolar replacement of 2 mM Tyr with 2 mM of a Tyr-dipeptide, such as Ala-Tyr and Gly-Tyr, showed a clear reduction in brown color towards an intensity classified as a 'normal brown color'.

TABLE 3

Effect on the brown colorization of different aqueous solutions containing tyrosine (Tyr) or Tyr-derivatives with or without riboflavin. Control solutions include the single amino acids glycine (Gly) and alanine (Ala) as well as the solvent ('solvent background', phosphate-buffered saline (PBS) or Minimal Essential Medium (MEM)). Brown color index: 0, no brown color; 1, week brown color; 2, moderate brown color; 3, normal brown color; 4, intensive brown color; 5, strong brown color

| Sample | | in PBS | | in cell culture media (MEM) | |
|---|---|---|---|---|---|
| | | Day 0 | Day 7 | Day 0 | Day 7 |
| with 0.013 mM riboflavin | 2 mM Tyr | 0 | 5 | 0 | 5 |
| | 2 mM Gly-Tyr | 0 | 3 | 0 | 3 |
| | 2 mM Ala-Tyr | 0 | 3 | 0 | 3 |
| | 32 mM Gly | 0 | 0 | 0 | 3 |
| | 32 mM Ala | 0 | 0 | 0 | 3 |
| | Solvent background | 0 | 0 | 0 | 3 |
| without 0.013 mM riboflavin | 2 mM Tyr | 0 | 0 | 0 | 2 |
| | 32 mM Gly-Tyr | 0 | 0 | 0 | 1 |
| | 32 mM Ala-Tyr | 0 | 0 | 0 | 1 |
| | 32 mM Ala | 0 | 0 | 0 | 1 |
| | 32 mM Gly | 0 | 0 | 0 | 1 |
| | Solvent background | 0 | 0 | 0 | 1 |

The invention claimed is:

1. A method for stabilizing a photosensitive composition, the method comprising: combining Ala-Tyr or Gly-Tyr, at a concentration in a range of from 0.5 to 20 mM, with a photosensitive composition comprising tryptophan in at least 2.5 mM, thereby stabilizing the photosensitive composition against brown coloration, wherein the photosensitive composition is an aqueous culture medium comprising a carbohydrate, a further free amino acid, an inorganic salt, a buffering agent, an/or a vitamin, wherein a molar ratio of the Ala-Tyr or Gly-Tyr to the tryptophan is in a range of from 0.2:1 to 8:1.

2. The method of claim 1, further comprising:

combining a cysteine derivative with the photosensitive composition.

3. The method of claim 1, wherein the photosensitive composition comprises cultured cells and is formed as a cell culture medium.

4. The method of claim 1, wherein the combining employs the Gly-Tyr.

5. The method of claim 1, wherein the combining employs the Ala-Tyr.

6. The method of claim 3, wherein the cultured cells are CHO cells, COS cells, VERO cells, BHK cells, HEK cells, HELA cells, AE-1 cells, NS0 cells, insect cells, algae cells, fibroblast cells, muscle cells, nerve cells, stem cells, skin cells, endothelial cells, immune cells, or hybridoma cells.

7. The method of claim 1, wherein the concentration of the Ala-Tyr or Gly-Tyr in the combining is in a range of from 0.5 to 10 mM.

8. The method of claim 1, wherein the aqueous culture medium comprises His, Ile, Leu, Lys, Met, Phe, Thr, Tyr, and Val.

9. The method of claim 1, wherein the free amino acid of the aqueous culture medium comprises glutamine at a higher concentration than other amino acids.

10. The method of claim 1, wherein the aqueous culture medium comprises glutamine, as the free amino acid, in a concentration of from 2.5 to 8 mM, and wherein a molar ratio of the Ala-Tyr or Gly-Tyr to the tryptophan is in a range of from 0.2:1 to 4:1.

11. The method of claim 1, wherein the aqueous culture medium is in 2 to 100-fold concentrated form.

12. The method of claim 1, wherein the combining reduces the brown coloration to no more than 77.8% of an absorbance in UV-vis at 330 nm of an otherwise identical aqueous culture medium without the Ala-Tyr or Gly-Tyr.

13. The method of claim 1, wherein the combining employs both the Ala-Tyr and the Gly-Tyr.

14. The method of claim 1, further comprising:

allowing the photosensitive composition to be exposed to daylight.

15. The method of claim 1, wherein the aqueous culture medium further comprises riboflavin.

16. The method of claim 1, wherein the aqueous culture medium further comprises a hexose.

17. The method of claim 1, wherein the combining is carried out for duration in a range of from 7 to 14 days.

18. The method of claim 1, wherein the combining is carried out for 7 days.

19. The method of claim 1, wherein the combining is carried out for 14 days.

* * * * *